United States Patent
Liao et al.

(10) Patent No.: US 12,421,533 B2
(45) Date of Patent: Sep. 23, 2025

(54) EAN B MUTANTS AND THEIR USES

(71) Applicant: Nanjing Nutrabuilding Bio-Tech Co., Ltd., Nanjing (CN)

(72) Inventors: Qilin Liao, Nanjing (CN); Jian Zhang, Nanjing (CN)

(73) Assignee: NANJING NUTRABUILDING BIO-TECH CO., LTD., Nanjing (CN)

( * ) Notice: Subject to any disclaimer, the term of this patent is extended or adjusted under 35 U.S.C. 154(b) by 663 days.

(21) Appl. No.: 17/761,157

(22) PCT Filed: Nov. 27, 2019

(86) PCT No.: PCT/CN2019/121260
§ 371 (c)(1),
(2) Date: Mar. 16, 2022

(87) PCT Pub. No.: WO2021/102736
PCT Pub. Date: Jun. 3, 2021

(65) Prior Publication Data
US 2023/0024648 A1    Jan. 26, 2023

(51) Int. Cl.
C12P 13/04     (2006.01)
C12N 9/10      (2006.01)
C12N 15/70     (2006.01)

(52) U.S. Cl.
CPC ............... *C12P 13/04* (2013.01); *C12N 9/13* (2013.01); *C12N 15/70* (2013.01); *C12N 2800/101* (2013.01)

(58) Field of Classification Search
CPC .......... C12P 13/04; C12N 9/13; C12N 15/70; C12N 2800/101; C12N 15/1024; C12N 17/10; C12N 15/52; C12N 15/74; C12N 1/20; C12N 15/63; C12N 1/205; C12N 9/1029; C12N 15/62; C12N 15/102; C12N 15/67; C12N 15/11; C12N 9/00; C12N 15/66; C12N 15/902; C12N 2800/22; C12N 15/10; C12N 15/00; C12N 7/00; C12N 15/86; C12N 15/64; C12N 15/09; C12N 9/52; C12N 15/79; C12N 9/0051; C12N 1/00; C12N 2830/55; C12N 15/71; C12N 15/1031; C12N 2510/00; C12N 2820/55; C12N 2800/00; C12N 2800/10; C12N 2810/55; C12N 2500/32; C07K 14/195; C07K 2319/00; C07K 19/00; C12Y 208/01
See application file for complete search history.

(56) References Cited

U.S. PATENT DOCUMENTS 11,098,330 B2 * 8/2021 Nakatani .................. C12N 1/20

FOREIGN PATENT DOCUMENTS

| WO | 2014100752 A1 | 6/2014 |
| WO | 2015168112 A1 | 11/2015 |
| WO | 2016121285 A1 | 8/2016 |
| WO | 2019163767 A1 | 8/2019 |

OTHER PUBLICATIONS

Burn R, Misson L, Meury M, Seebeck FP. Anaerobic Origin of Ergothioneine. Angew Chem Int Ed Engl. Oct. 2, 2017;56(41):12508-12511. doi: 10.1002/anie.201705932. Epub Sep. 1, 2017. PMID: 28786519. (Year: 2017).*
Wilson DS, Keefe AD. Random mutagenesis by PCR. Curr Protoc Mol Biol. May 2001;Chapter 8: Unit8.3. doi: 10.1002/0471142727.mb0803s51. PMID: 18265275. (Year: 2001).*
McCullum, E.O., Williams, B.A.R., Zhang, J., Chaput, J.C. (2010). Random Mutagenesis by Error-Prone PCR. In: Braman, J. (eds) In Vitro Mutagenesis Protocols. Methods in Molecular Biology, vol. 634. Humana Press, Totowa, NJ. https://doi.org/10.1007/978-1-60761-652-8_7 (Year: 2010).*
Carter P. Site-directed mutagenesis. Biochem J. Jul. 1, 1986;237(1):1-7. doi: 10.1042/bj2370001. PMID: 3541892; PMCID: PMC1146940. (Year: 1986).*
Ventura AM, Villa LL. Plasmid pSH: a strong mammalian expression vector. Biochem Biophys Res Commun. Apr. 30, 1993;192(2):867-9. doi: 10.1006/bbrc.1993.1495. PMID: 8387291. (Year: 1993).*
Livingstone CD, Barton GJ. Protein sequence alignments: a strategy for the hierarchical analysis of residue conservation. Comput Appl Biosci. Dec. 1993;9(6):745-56. doi: 10.1093/bioinformatics/9.6.745. PMID: 8143162. (Year: 1993).*
Leisinger F, Burn R, Meury M, Lukat P, Seebeck FP. Structural and Mechanistic Basis for Anaerobic Ergothioneine Biosynthesis. J Am Chem Soc. May 1, 2019;141(17):6906-6914. doi: 10.1021/jacs.8b12596. Epub Apr. 23, 2019. PMID: 30943021. (Year: 2019).*
Leisinger. F. et al. "Structural and Mechanistic Basis for Anaerobic Ergothioneine Biosynthesis" Journal of the American Chemical Society, vol. 141. Apr. 3, 2019 (Apr. 3, 2019).
Jones. G.W. et al. "The evolutionary history of the genes involved in the biosynthesis of the antioxidant ergothioneine" Gene, vol. 549, Jul. 26, 2014 (Jul. 26, 2014).
Lucas, S. et al. "Rhodanese domain protien[Chlorobium limicola DSM245] GenBank:ACD90218. I" Genbank, Sep. 10, 2019 (Sep. 10, 2019).

* cited by examiner

Primary Examiner — Robert B Mondesi
Assistant Examiner — Alexander B Pastora
(74) Attorney, Agent, or Firm — ANOVA LAW GROUP, PLLC

(57) ABSTRACT

Provided herein includes a method for producing ergothioneine, comprising N(α)-trimethyl histidine and an oxidative sulfurizing enzyme mutant. With the mutant enzyme's help, the conversion rate is higher than 30% with the mutant enzyme amount of 8000/g substrate in 24 hours. Disclosed are a nucleic acid encoding the mutant enzyme, an expression vector comprising the nucleic acid, an expressing host comprising the nucleic acid or the expression vector, and the use of the mutant enzyme EanB for producing the ergothioneine.

13 Claims, No Drawings
Specification includes a Sequence Listing.

SEQUENCE LISTING

<160> NUMBER OF SEQ ID NOS: 8

<210> SEQ ID NO 1
<211> LENGTH: 457
<212> TYPE: PRT
<213> ORGANISM: Chlorobium limicola

<400> SEQUENCE: 1

Met Gln Asn Lys Asn Phe Arg Ala Pro Gln Ser Glu Ala Ile Gly Ile
1               5                   10                  15

Leu Tyr Lys Leu Ile Glu Thr Gly Ser Lys His Lys Asn Met Tyr Asp
            20                  25                  30

His Thr Glu Ile Thr Thr Asp Ser Leu Leu Ala Leu Leu Gly Ser Glu
        35                  40                  45

Lys Val Lys Ile Ile Asp Val Arg Ser Ala Asp Ala Tyr Asn Gly Trp
    50                  55                  60

Arg Met Arg Gly Glu Val Arg Gly Gly His Ile Lys Gly Ala Lys Ser
65                  70                  75                  80

Leu Pro Ala Lys Trp Leu Thr Asp Pro Glu Trp Leu Asn Ile Val Arg
                85                  90                  95

Phe Lys Gln Ile Arg Pro Glu Asp Ala Ile Val Leu Tyr Gly Tyr Thr
            100                 105                 110

Pro Glu Glu Cys Glu Gln Thr Ala Thr Arg Phe Lys Glu Asn Gly Tyr
        115                 120                 125

Asn Asn Val Ser Val Phe His Arg Phe His Pro Asp Trp Thr Gly Asn
    130                 135                 140

Asp Ala Phe Pro Met Asp Arg Leu Glu Gln Tyr Asn Arg Leu Val Pro
145                 150                 155                 160

Ala Glu Trp Val Asn Gly Leu Ile Ser Gly Glu Ile Pro Glu Tyr
                165                 170                 175

Asp Asn Asp Thr Phe Ile Val Cys His Ala His Tyr Arg Asn Arg Asp
            180                 185                 190

Ala Tyr Leu Ser Gly His Ile Pro Gly Ala Thr Asp Met Asp Thr Leu
        195                 200                 205

Ala Leu Glu Ser Pro Glu Thr Trp Asn Arg Arg Thr Pro Glu Glu Leu
    210                 215                 220

Lys Lys Ala Leu Glu Glu His Gly Ile Thr Ala Ser Thr Thr Val Val
225                 230                 235                 240

Leu Tyr Gly Lys Phe Met His Pro Asp Asn Ala Asp Glu Phe Pro Gly
                245                 250                 255

Ser Ala Ala Gly His Ile Gly Ala Ile Arg Leu Ala Phe Ile Met Met

```
            260             265             270
Tyr Ala Gly Val Glu Asp Val Arg Val Leu Asn Gly Gly Tyr Gln Ser
        275                 280                 285

Trp Thr Asp Ala Gly Phe Ala Ile Ser Lys Asp Asp Val Pro Lys Thr
    290                 295                 300

Thr Val Pro Glu Phe Gly Ala Pro Ile Pro Ser Arg Pro Glu Phe Ala
305                 310                 315                 320

Val Asp Ile Asp Glu Ala Lys Glu Met Leu Gln Ser Glu Asp Ser Asp
                325                 330                 335

Leu Val Cys Val Arg Ser Tyr Pro Glu Tyr Ile Gly Glu Val Ser Gly
            340                 345                 350

Tyr Asn Tyr Ile Lys Lys Lys Gly Arg Ile Pro Gly Ala Ile Phe Ala
        355                 360                 365

Glu Cys Gly Ser Asp Ala Tyr His Met Glu Asn Tyr Arg Asn His Asp
    370                 375                 380

His Thr Thr Arg Glu Tyr His Glu Ile Glu Asp Ile Trp Ala Lys Ser
385                 390                 395                 400

Gly Ile Ile Pro Lys Lys His Leu Ala Phe Tyr Cys Gly Thr Gly Trp
                405                 410                 415

Arg Gly Ser Glu Ala Trp Phe Asn Ala Leu Leu Met Gly Trp Pro Arg
            420                 425                 430

Val Ser Val Tyr Asp Gly Gly Trp Phe Glu Trp Ser Asn Asp Pro Glu
        435                 440                 445

Asn Pro Tyr Glu Thr Gly Val Pro Lys
    450                 455

<210> SEQ ID NO 2
<211> LENGTH: 1374
<212> TYPE: DNA
<213> ORGANISM: Chlorobium limicola

<400> SEQUENCE: 2
atgcagaaca aaactttcg  tgcaccgcag agcgaggcaa ttggcattct gtacaagctg      60
atcgagaccg gcagcaagca taagaacatg tacgaccaca ccgaaattac aaccgacagt    120
ctgctggctt tactgggtag cgaaaaagtg aaaatcatcg acgtgcgtag cgcagatgcc    180
tacaacggtt ggcgtatgcg tggtgaagtg cgtggtggtc atattaaggg cgccaaatct    240
ttaccggcaa agtggctgac agacccggaa tggctgaata ttgtgcgttt caaacagatt    300
cgcccggagg acgcaatcgt tctgtacggc tatacccccgg aagaatgcga acagaccgca    360
acccgcttca aggaaaatgg ttacaataac gtgagcgttt tcaccgcttt tcacccggat    420
tggaccggta acgacgcctt tccgatggat cgtttagaac agtataaccg tctggttccc    480
gctgaatggg tgaacggtct gatcagcggt gaggaaatcc ggaatacga taacgacacc    540 ttcatcgtgt gccatgccca ctatcgcaac cgtgatgcct atctgagcgg tcacattccg    600
ggtgccaccg atatggatac tttagcttta gaaagccccg aaacatggaa tcgccgcaca    660
cccgaagaac tgaaaaaggc tttagaagag cacggcatta ccgccagcac acagttgtg    720 ctgtacggca agttcatgca tccggataac gccgacgaat tccgggtag tgccgctggt    780 catattggtg ccatccgttt agcctttatc atgatgtacg ccggcgtgga agatgttcgc    840
gtgctgaatg cggttatca  gagttggacc gacgccggct ttgcaattag caaagacgat    900
gtgccgaaaa ccaccgttcc ggagtttggt gccccgattc cgagtcgccc ggaatttgca    960
gtggacattg acgaggccaa ggaaatgtta caaagcgaag acagcgatct ggtgtgtgtg   1020
```

```
cgcagttatc cggagtacat cggcgaggtt agcggttaca actatattaa gaagaaaggc    1080 cgtattccg  gtgccatctt cgccgaatgc ggtagcgatg cctaccacat ggagaattac    1140
cgcaaccacg accataccac acgcgaatac catgagatcg aggacatctg gccaaaagc     1200 ggcattattc  cgaagaaaca tttagccttt tattgcggca ccggttggcg tggtagcgag   1260
gcttggttca  atgctttatt aatgggctgg cctcgtgtta gcgtgtatga cggtggctgg   1320
tttgagtgga gtaatgaccc ggagaaccct tatgaaaccg cgtgcctaa ataa           1374
```

<210> SEQ ID NO 3
<211> LENGTH: 457
<212> TYPE: PRT
<213> ORGANISM: Artificial Sequence
<220> FEATURE:
<223> OTHER INFORMATION: The amino acid sequence of an EanB-888 mutant

<400> SEQUENCE: 3

```
Met Gln Asn Lys Asn Phe Arg Ala Pro Gln Ser Glu Ala Ile Gly Ile
1               5                   10                  15

Leu Tyr Lys Leu Ile Glu Thr Gly Ser Lys His Lys Asn Met Tyr Asp
            20                  25                  30

His Thr Glu Ile Thr Thr Asp Ser Leu Leu Ala Leu Leu Gly Ser Glu
        35                  40                  45

Lys Val Lys Ile Ile Asp Val Arg Ser Ala Asp Ala Tyr Asn Gly Trp
    50                  55                  60

Arg Met Arg Gly Glu Val Arg Gly Gly His Arg Lys Gly Ala Lys Ser
65                  70                  75                  80

Leu Pro Ala Lys Trp Leu Thr Asp Pro Glu Trp Leu Asn Ile Val Arg
                85                  90                  95

Phe Lys Gln Ile Arg Pro Glu Asp Ala Ile Val Leu Tyr Gly Tyr Thr
            100                 105                 110

Pro Glu Glu Cys Glu Gln Thr Ala Thr Arg Phe Lys Glu Asn Gly Tyr
        115                 120                 125

Asn Asn Val Ser Val Phe His Arg Phe His Pro Asp Trp Thr Gly Asn
    130                 135                 140

Asp Ala Phe Pro Met Asp Arg Leu Glu Gln Tyr Asn Arg Leu Val Pro
145                 150                 155                 160

Ala Glu Trp Val Asn Gly Leu Ile Ser Gly Glu Glu Ile Pro Glu Tyr
                165                 170                 175

Asp Asn Asp Thr Phe Ile Val Cys His Ala His Tyr Arg Asn Arg Asp
            180                 185                 190

Ala Tyr Leu Ser Gly His Ile Pro Gly Ala Thr Asp Met Asp Thr Leu
        195                 200                 205

Ala Leu Glu Ser Pro Glu Thr Trp Asn Arg Arg Thr Pro Glu Glu Leu
    210                 215                 220

Lys Lys Ala Leu Glu Glu His Gly Ile Thr Ala Ser Thr Thr Val Val
225                 230                 235                 240

Leu Tyr Gly Lys Phe Met His Pro Asp Asn Ala Asp Glu Phe Pro Gly
                245                 250                 255

Ser Ala Ala Gly His Ile Gly Ala Ile Arg Leu Ala Phe Ile Met Met
            260                 265                 270

Tyr Ala Gly Val Glu Asp Val Arg Val Leu Asn Gly Gly Tyr Gln Ser
        275                 280                 285

Trp Thr Asp Ala Gly Phe Ala Ile Ser Lys Asp Asp Val Pro Lys Thr
    290                 295                 300
```

Thr Val Pro Glu Phe Gly Ala Pro Ile Pro Ser Arg Pro Glu Phe Ala
305                 310                 315                 320

Val Asp Ile Asp Glu Ala Lys Glu Met Leu Gln Ser Glu Asp Ser Asp
                325                 330                 335

Leu Val Cys Val Arg Ser Tyr Pro Glu Tyr Ile Gly Val Ser Gly
            340                 345                 350

Tyr Asn Tyr Ile Lys Lys Lys Gly Arg Ile Pro Gly Ala Ile Phe Ala
        355                 360                 365

Pro Cys Gly Ser Asp Ala Tyr His Met Glu Asn Tyr Arg Asn His Asp
    370                 375                 380

His Thr Thr Arg Glu Tyr His Glu Ile Glu Asp Ile Trp Ala Lys Ser
385                 390                 395                 400

Gly Ile Ile Pro Lys Lys His Leu Ala Phe Tyr Cys Gly Thr Gly Trp
                405                 410                 415

Arg Gly Ser Glu Ala Trp Phe Asn Ala Leu Leu Met Gly Trp Pro Arg
            420                 425                 430

Val Ser Val Tyr Asp Gly Gly Trp Phe Glu Trp Ser Asn Asp Pro Glu
        435                 440                 445

Asn Pro Tyr Glu Thr Gly Val Pro Lys
    450                 455

<210> SEQ ID NO 4
<211> LENGTH: 1374
<212> TYPE: DNA
<213> ORGANISM: Artificial Sequence
<220> FEATURE:
<223> OTHER INFORMATION: The nucleic acid sequence of an EanB-888 mutant

<400> SEQUENCE: 4
atgcagaaca aaactttcg tgcaccgcag agcgaggcaa ttggcattct gtacaagctg      60
atcgagaccg gcagcaagca taagaacatg tacgaccaca ccgaaattac aaccgacagt     120
ctgctggctt tactgggtag cgaaaaagtg aaaatcatcg acgtgcgtag cgcagatgcc     180
tacaacggtt ggcgtatgcg tggtgaagtg cgtggtggtc atagaaaggg cgccaaatct     240
ttaccggcaa agtggctgac agacccggaa tggctgaata ttgtgcgttt caaacagatt     300
cgcccggagg acgcaatcgt tctgtacggc tataccccgg aagaatgcga acagaccgca     360
acccgcttca aggaaaatgg ttacaataac gtgagcgttt tcaccgctt tcacccggat      420 tggaccggta cgacgccctt ccgatggat cgtttagaac agtataaccg tctggttccc      480
gctgaatggg tgaacggtct gatcagcggt gaggaaatcc ggaatacga taacgacacc     540 ttcatcgtgt gccatgccca ctatcgcaac cgtgatgcct atctgagcgg tcacattccg     600
ggtgccaccg atatggatac tttagcttta gaaagccccg aaacatggaa tcgccgcaca     660
cccgaagaac tgaaaaaggc tttagaagag cacggcatta ccgccagcac cacagttgtg     720
ctgtacggca gttcatgca tccggataac gccgacgaat tccgggtag tgccgctggt      780 catattggtg ccatccgttt agcctttatc atgatgtacg ccggcgtgga agatgttcgc     840
gtgctgaatg gcggttatca gagttggacc gacgccggct ttgcaattag caaagacgat     900
gtgccgaaaa ccaccgttcc ggagtttggt gccccgattc cgagtcgccc ggaatttgca     960
gtggacattg acgaggccaa ggaaatgtta caaagcgaag acagcgatct ggtgtgtgtg    1020
cgcagttatc cggagtacat cggcgaggtt agcggttaca actatattaa gaagaaaggc    1080
cgtattcccg gtgccatctt cgccccatgc ggtagcgatg cctaccacat ggagaattac    1140

-continued

```
cgcaaccacg accataccac acgcgaatac catgagatcg aggacatctg ggccaaaagc      1200
ggcattattc cgaagaaaca tttagccttt tattgcggca ccggttggcg tggtagcgag      1260
gcttggttca atgctttatt aatgggctgg cctcgtgtta gcgtgtatga cggtggctgg      1320
tttgagtgga gtaatgaccc ggagaaccct tatgaaaccg gcgtgcctaa ataa            1374
```

```
<210> SEQ ID NO 5
<211> LENGTH: 457
<212> TYPE: PRT
<213> ORGANISM: Artificial Sequence
<220> FEATURE:
<223> OTHER INFORMATION: The amino acid sequence of an EanB-19 mutant

<400> SEQUENCE: 5

Met Gln Asn Lys Asn Phe Arg Ala Pro Gln Ser Glu Ala Ile Gly Ile
1               5                   10                  15

Leu Tyr Lys Leu Ile Glu Thr Gly Ser Lys His Lys Asn Met Tyr Asp
                20                  25                  30

His Thr Glu Ile Thr Thr Asp Ser Leu Leu Ala Leu Leu Gly Ser Glu
            35                  40                  45

Lys Val Lys Ile Ile Asp Val Arg Ser Ala Asp Ala Tyr Asn Gly Trp
        50                  55                  60

Arg Met Arg Gly Glu Val Arg Gly Gly His Arg Lys Gly Ala Lys Ser
65                  70                  75                  80

Leu Pro Ala Lys Trp Leu Thr Asp Pro Glu Trp Leu Asn Ile Val Arg
                85                  90                  95

Phe Lys Gln Ile Arg Pro Glu Asp Ala Ile Val Leu Tyr Gly Tyr Thr
            100                 105                 110

Pro Glu Glu Cys Glu Gln Thr Ala Thr Arg Phe Lys Glu Asn Gly Tyr
        115                 120                 125

Asn Asn Val Ser Val Phe His Arg Phe His Pro Asp Trp Thr Gly Asn
130                 135                 140

Asp Ala Phe Pro Met Asp Arg Leu Glu Gln Tyr Asn Arg Leu Val Pro
                145                 150                 155                 160

Ala Glu Trp Val Asn Gly Leu Ile Ser Gly Glu Glu Ile Pro Glu Tyr
            165                 170                 175

Asp Asn Asp Thr Phe Ile Val Cys His Ala His Tyr Arg Asn Arg Asp
        180                 185                 190

Ala Tyr Leu Ser Gly His Ile Pro Gly Ala Thr Asp Met Asp Thr Leu
    195                 200                 205

Ala Leu Glu Ser Pro Glu Thr Trp Asn Arg Arg Thr Pro Glu Glu Leu
210                 215                 220

Lys Lys Ala Leu Glu Glu His Gly Ile Thr Ala Ser Thr Thr Val Val
225                 230                 235                 240

Leu Tyr Gly Lys Phe Met His Pro Asp Asn Ala Asp Glu Phe Pro Gly
                245                 250                 255

Ser Ala Ala Gly His Ile Gly Ala Ile Arg Leu Ala Phe Ile Met Met
            260                 265                 270

Tyr Ala Gly Val Glu Asp Val Arg Val Leu Asn Gly Gly Tyr Gln Ser
        275                 280                 285

Trp Thr Asp Ala Gly Phe Ala Ile Ser Lys Asp Val Pro Lys Thr
    290                 295                 300

Thr Val Pro Glu Phe Gly Ala Pro Ile Pro Ser Arg Pro Glu Phe Ala
305                 310                 315                 320

Val Asp Ile Asp Glu Ala Lys Glu Met Leu Gln Ser Glu Asp Ser Asp
```

```
                      325                 330                 335
Leu Val Cys Val Arg Ser Tyr Pro Glu Tyr Ile Gly Glu Val Ser Gly
            340                 345                 350
Tyr Asn Tyr Ile Lys Lys Lys Gly Arg Ile Pro Gly Ala Ile Phe Ala
                355                 360                 365
Glu Cys Gly Ser Asp Ala Tyr His Met Glu Asn Tyr Arg Asn His Asp
        370                 375                 380
His Thr Thr Arg Glu Tyr His Glu Ile Glu Asp Ile Trp Ala Lys Ser
385                 390                 395                 400
Gly Ile Ile Pro Lys Lys His Leu Ala Phe Tyr Cys Gly Thr Gly Trp
                405                 410                 415
Arg Gly Ser Glu Ala Trp Phe Asn Ala Leu Leu Met Gly Trp Pro Arg
            420                 425                 430
Val Ser Val Tyr Asp Gly Gly Trp Phe Glu Trp Ser Asn Asp Pro Glu
                435                 440                 445
Asn Pro Tyr Glu Thr Gly Val Pro Lys
    450                 455
```

<210> SEQ ID NO 6
<211> LENGTH: 1374
<212> TYPE: DNA
<213> ORGANISM: Artificial Sequence
<220> FEATURE:
<223> OTHER INFORMATION: The nucleic acid sequence of an EanB-19 mutant

<400> SEQUENCE: 6

```
atgcagaaca aaactttcg tgcaccgcag agcgaggcaa ttggcattct gtacaagctg      60
atcgagaccg gcagcaagca taagaacatg tacgaccaca ccgaaattac aaccgacagt     120
ctgctggctt tactgggtag cgaaaaagtg aaaatcatcg acgtgcgtag cgcagatgcc     180
tacaacggtt ggcgtatgcg tggtgaagtg cgtggtggtc atcgtaaggg cgccaaatct     240
ttaccggcaa agtggctgac agacccggaa tggctgaata ttgtgcgttt caaacagatt     300
cgccccggagg acgcaatcgt tctgtacggc tataccccgg agaatgcga acagaccgca     360
acccgcttca aggaaaatgg ttacaataac gtgagcgttt tcaccgcctt cacccggat     420
tggaccggta acgacgcctt ccgatggat cgtttagaac agtataaccg tctggttccc     480
gctgaatggg tgaacggtct gatcagcggt gaggaaatcc ggaatacga taacgacacc     540
ttcatcgtgt gccatgccca ctatcgcaac cgtgatgcct atctgagcgg tcacattccg     600
ggtgccaccg atatggatac tttagcttta gaaagccccg aaacatggaa tcgccgcaca     660
cccgaagaac tgaaaaaggc tttagaagag cacggcatta ccgccagcac cacagttgtg     720
ctgtacggca gttcatgca tccggataac gccgacgaat tccgggtag tgccgctggt     780
catattggtg ccatccgttt agcctttatc atgatgtacg ccggcgtgga agatgttcgc     840
gtgctgaatg gcggttatca gagttggacc gacgccggct ttgcaattag caaagacgat     900
gtgccgaaaa ccaccgttcc ggagtttggt gccccgattc cgagtcgccc ggaatttgca     960
gtggacattg acgaggccaa ggaaatgtta caaagcgaag acagcgatct ggtgtgtgtg    1020
cgcagttatc cggagtacat cggcgaggtt agcggttaca actatattaa gaagaaaggc    1080
cgtattcccg gtgccatctt cgccgaatgc ggtagcgatg cctaccacat ggagaattac    1140
cgcaaccacg accataccac acgcgaatac catgagatcg aggacatctg gccaaaagc    1200
ggcattattc cgaagaaaca tttagccttt tattgcggca ccggttggcg tggtagcgag    1260
gcttggttca atgctttatt aatgggctgg cctcgtgtta gcgtgtatga cggtggctgg    1320
```

```
tttgagtgga gtaatgaccc ggagaaccct tatgaaaccg gcgtgcctaa ataa        1374
```

<210> SEQ ID NO 7
<211> LENGTH: 457
<212> TYPE: PRT
<213> ORGANISM: Artificial Sequence
<220> FEATURE:
<223> OTHER INFORMATION: The amino acid sequence of an EanB-665 mutant

<400> SEQUENCE: 7

```
Met Gln Asn Lys Asn Phe Arg Ala Pro Gln Ser Glu Ala Ile Gly Ile
1               5                   10                  15

Leu Tyr Lys Leu Ile Glu Thr Gly Ser Lys His Lys Asn Met Tyr Asp
            20                  25                  30

His Thr Glu Ile Thr Thr Asp Ser Leu Leu Ala Leu Leu Gly Ser Glu
        35                  40                  45

Lys Val Lys Ile Ile Asp Val Arg Ser Ala Asp Ala Tyr Asn Gly Trp
    50                  55                  60

Arg Met Arg Gly Glu Val Arg Gly Gly His Ile Lys Gly Ala Lys Ser
65                  70                  75                  80

Leu Pro Ala Leu Trp Leu Thr Asp Pro Glu Trp Leu Asn Ile Val Arg
                85                  90                  95

Phe Lys Gln Ile Arg Pro Glu Asp Ala Ile Val Leu Tyr Gly Tyr Thr
            100                 105                 110

Pro Glu Glu Cys Glu Gln Thr Ala Thr Arg Phe Lys Glu Asn Gly Tyr
        115                 120                 125

Asn Asn Val Ser Val Phe His Arg Phe His Pro Asp Trp Thr Gly Asn
    130                 135                 140

Asp Ala Phe Pro Met Asp Arg Leu Glu Gln Tyr Asn Arg Leu Val Pro
145                 150                 155                 160

Ala Glu Trp Val Asn Gly Leu Ile Ser Gly Glu Glu Ile Pro Glu Tyr
                165                 170                 175

Asp Asn Asp Thr Phe Ile Val Cys His Ala His Tyr Arg Asn Arg Asp
            180                 185                 190

Ala Tyr Leu Ser Gly His Ile Pro Gly Ala Thr Asp Met Asp Thr Leu
        195                 200                 205

Ala Leu Glu Ser Pro Glu Thr Trp Asn Arg Arg Thr Pro Glu Glu Leu
    210                 215                 220

Lys Lys Ala Leu Glu Glu His Gly Ile Thr Ala Ser Thr Thr Val Val
225                 230                 235                 240

Leu Tyr Gly Lys Phe Met His Pro Asp Asn Ala Asp Glu Phe Pro Gly
                245                 250                 255

Ser Ala Ala Gly His Ile Gly Ala Ile Arg Leu Ala Phe Ile Met Met
            260                 265                 270

Tyr Ala Gly Val Glu Asp Val Arg Val Leu Asn Gly Gly Tyr Gln Ser
        275                 280                 285

Trp Thr Asp Ala Gly Phe Ala Ile Ser Lys Asp Asp Val Pro Lys Thr
    290                 295                 300

Thr Val Pro Glu Phe Gly Ala Pro Ile Pro Ser Arg Pro Glu Phe Ala
305                 310                 315                 320

Val Asp Ile Asp Glu Ala Lys Glu Met Leu Gln Ser Glu Asp Ser Asp
                325                 330                 335

Leu Val Cys Val Arg Ser Tyr Pro Glu Tyr Ile Gly Gly Val Ser Gly
            340                 345                 350
```

```
Tyr Asn Tyr Ile Lys Lys Gly Arg Ile Pro Gly Ala Ile Phe Ala
            355                 360                 365

Pro Cys Gly Ser Asp Ala Tyr His Met Glu Asn Tyr Arg Asn His Asp
    370                 375                 380

His Thr Thr Arg Glu Tyr His Glu Ile Glu Asp Ile Trp Ala Lys Ser
385                 390                 395                 400

Gly Ile Ile Pro Lys Lys His Leu Ala Phe Tyr Cys Gly Thr Gly Trp
                405                 410                 415

Arg Gly Ser Glu Ala Trp Phe Asn Ala Leu Leu Met Gly Trp Pro Arg
            420                 425                 430

Val Ser Val Tyr Asp Gly Gly Trp Phe Glu Trp Ser Asn Asp Pro Glu
        435                 440                 445

Asn Pro Tyr Glu Thr Gly Val Pro Lys
    450                 455
```

<210> SEQ ID NO 8
<211> LENGTH: 1374
<212> TYPE: DNA
<213> ORGANISM: Artificial Sequence
<220> FEATURE:
<223> OTHER INFORMATION: The nucleic acid sequence of an EanB-665 mutant

<400> SEQUENCE: 8

```
atgcagaaca aaactttcg tgcaccgcag agcgaggcaa ttggcattct gtacaagctg      60
atcgagaccg gcagcaagca taagaacatg tacgaccaca ccgaaattac aaccgacagt     120
ctgctggctt tactgggtag cgaaaaagtg aaaatcatcg acgtgcgtag cgcagatgcc    180
tacaacggtt ggcgtatgcg tggtgaagtg cgtggtggtc atattaaggg cgccaaatct    240
ttaccggcat tgtggctgac agacccggaa tggctgaata ttgtgcgttt caaacagatt    300
cgcccggagg acgcaatcgt tctgtacggc tataccccgg aagaatgcga acagaccgca    360
acccgcttca ggaaaatgg ttacaataac gtgagcgttt tcaccgctt tcacccggat     420 tggaccggta acgacgcctt tccgatggat cgtttagaac agtataaccg tctggttccc    480
gctgaatggg tgaacggtct gatcagcggt gaggaaatcc cggaatacga taacgacacc    540
ttcatcgtgt gccatgccca ctatcgcaac cgtgatgcct atctgagcgg tcacattccg    600
ggtgccaccg atatggatac tttagctta gaaagccccg aaacatggaa tcgccgcaca     660
cccgaagaac tgaaaaaggc tttagaagag cacggcatta ccgccagcac acagttgtg     720 ctgtacggca agttcatgca tccggataac gccgacgaat tccgggtag tgccgctggt     780 catattggtg ccatccgttt agcctttatc atgatgtacg ccggcgtgga agatgttcgc    840
gtgctgaatg gcggttatca gagttggacc gacgccggct ttgcaattag caaagacgat    900
gtgccgaaaa ccaccgttcc ggagtttggt gccccgattc cgagtcgccc ggaatttgca    960
gtggacattg acgaggccaa ggaaatgtta caaagcgaag acagcgatct ggtgtgtgtg    1020
cgcagttatc cggagtacat cggcgaggtt agcggttaca actatattaa gaagaaaggc    1080
cgtattcccg gtgccatctt cgccccatgc ggtagcgatg cctaccacat ggagaattac    1140
cgcaaccacg accataccac acgcgaatac catgagatcg aggacatctg gccaaaagc    1200 ggcattattc cgaagaaaca tttagccttt tattgcggca ccggttggcg tggtagcgag    1260
gcttggttca atgctttatt aatgggctgg cctcgtgtta gcgtgtatga cggtggctgg    1320
tttgagtgga gtaatgaccc ggagaaccct tatgaaaccg gcgtgcctaa ataa          1374
```

EAN B MUTANTS AND THEIR USES

CROSS-REFERENCE TO RELATED APPLICATION

This application is the US national phase of International Application No. PCT/CN2019/121260, filed on Nov. 27, 2019, the contents of which are incorporated herein by reference in their entirety.

REFERENCE TO AN ELECTRONIC SEQUENCE LISTING

The contents of the electronic sequence listing (Name: U.S. Ser. No. 17/761,157-20220817-revised_Sequence-listings_VP172651-018400.txt; Size: 60 kilobytes; and Date of Creation: Mar. 16, 2022) are herein incorporated by reference in its entirety.

FIELD OF THE DISCLOSURE

The present invention relates to molecular biology, and specifically relates to mutants of enzyme EanB from the green sulfur bacterium *Chlorobium limicola* and their uses.

BACKGROUND

L-ergothioneine (EGT), has the following structure:

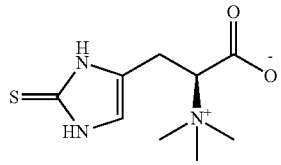

EGT is the only natural 2-thioimidazole amino acid known until now. It has many physiological effects such as anti-oxidation, anti-inflammatory, prolonging cell life cycle and anti-cell aging activity, and nerve cell production improvement. At the same time, it has efficacy in protecting cells and fighting damage in a variety of disease models including complications such as Alzheimer's disease and diabetes. Therefore, EGT has a good market application prospect.

Currently, EGT can be obtained by chemical synthesis, edible fungi extraction and microbial fermentation. A variety of microorganisms have been confirmed to be used to synthesize EGT, such as mycobacteria, *Streptomyces*, molds, yeast and so on. Among them, the biosynthesis of EGT by edible fungus mycelium deep-fermentation technology is a mainstream direction for low-cost and large-scale production of EGT.

However, there are two important defects in the edible fungus mycelium deep-fermentation technology. Firstly, the growth rate of edible fungus mycelium is slow, resulting in a longer fermentation cycle for generally 7-10 days. Secondly, the EGT synthesized by edible fungus fermentation is mostly accumulated inside the mycelium, which requires a complicated post-treatment process of mycelium like crushing and extraction. This results in a relatively high production cost. Therefore, a method which can easily and quickly produce EGT at a low cost is urgently required.

SUMMARY OF THE DISCLOSURE

The objects of the present invention are to provide an EanB enzyme mutant, a nucleic acid sequence encoding the EanB enzyme mutant, a recombinant expression vector comprising the nucleic acid sequence, an expressing host comprising the nucleic acid sequence or the recombinant expression vector, and uses of the EanB enzyme mutants, especially the use of the enzyme Ean B mutant to produce ergothioneine.

In this invention, the enzyme EanB was obtained from the green sulfur bacterium *Chlorobium limicola*. This enzyme can catalyze oxidative sulfurization of N(α)-trimethyl histidine. Under anaerobic condition, enzyme EanB catalyzes 6-site C to form C—S bond and synthesize ergothioneine by one-step (Reto, B., et al. (2017). "Anaerobic Origin of Ergothioneine." Angewandte Chemie International Edition 56(41): 12508-12511; Leisinger, F., et al. (2019). "Structural and Mechanistic Basis for Anaerobic Ergothioneine Biosynthesis." Journal of the American Chemical Society 141(17): 6906-6914).

Based on wild-type enzyme EanB, the EanB gene mutation library was construction by error-prone PCR mutagenesis. Three sites that can enhance enzyme activity were then screened out. An EanB enzyme mutant with significantly improved activity was obtained by site-directed mutagenesis at last.

The present invention relates to the following aspects:

In an embodiment, the present invention provides an EanB enzyme mutant, which comprises mutation of one or more mutants at position 75, 84 or 369 in amino acid sequence of SEQ ID No 1.

In another preferred embodiment, the mutation is one or two of the following changes: (1) the I of position 75 is mutated to R; (2) the E of position 369 is mutated to P.

In particular preferred embodiments, the mutant comprises the amino acid sequence according to any one of SEQ ID NO: 3, 5, or 7.

In an embodiment, the polynucleotide encoding the EanB enzyme mutant of the invention, and the polynucleotide comprises the nucleic acid sequence according to any one of SEQ ID NO: 4, 6, or 8.

In an embodiment, a mutant expression vector comprising the polynucleotide according to any one of SEQ ID NO: 4, 6, or 8.

Preferably, the vector is pSH plasmid comprising the polynucleotide according to any one of SEQ ID NO: 4, 6, or 8.

In an embodiment, a host cell comprising the polynucleotide encoding the EanB enzyme mutant according to any one of SEQ ID NO: 4, 6, or 8.

In a preferred embodiment, a host cell comprising the vector comprising the polynucleotide according to any one of SEQ ID NO: 4, 6, or 8.

Preferably, the host cell is *Escherichia coli*.

The invention also includes the use of the EanB enzyme mutant, preferably, the use of the EanB enzyme mutant of this invention is to produce ergothioneine.

DETAILED DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated and/or described, and should not be construed to limit the scope or breadth of the present disclosure. The headings used throughout this disclosure are provided for convenience only and are not to be construed to limit the claims in any way. Embodiments illustrated under any heading may be combined with embodiments illustrated under any other heading.

The present invention relates to the addition amount, content and concentration of various substances, wherein the percentages are referred to as mass percentages unless otherwise specified. In the examples of the present invention, the temperature generally means room temperature (15-25° C.) if there is no specific explanation made for the reaction temperature or the operating temperature.

In the present invention, enzyme Ean B (or EanB) may be abbreviated as "Ean B" or described as "oxidative sulfurizing enzyme Ean B."

In the present invention, the terms "wild type", "wild enzyme", and "wild-type enzyme" have the same meaning and refer to the oxidative sulfurizing enzyme EanB (SEQ ID NO: 1) which has not been genetically engineered.

In order to obtain an Ean B mutant with higher enzymatic activity, the present invention performs point mutation of the wild type oxidative sulfurizing enzyme EanB gene sequence SEQ ID NO: 2. The amino acid sequence of one or more amino acid site-substituted mutants was obtained by error-prone PCR technology, three sites for enhancing enzyme activity were screened out, and then one Ean B mutant with significantly improved enzyme activity was obtained by site-directed mutagenesis.

Since the Ean B mutant of the present invention is clear in amino acid sequence, a gene encoding the mutant, an expression assay and plasmid containing the gene, and a transformant comprising the plasmid are easily obtained by those skilled in the art. These genes, expression assays, plasmids, transformants can be obtained by genetic engineering construction methods well known to those skilled in the art.

The transformant host may be any microorganism suitable for expressing an oxidative sulfide enzyme mutant, including bacteria and fungi. Preferably, the microorganisms are *Escherichia coli, Pichia pastoris, Saccharomyces cerevisiae,* or *Bacillus subtilis,* preferably *Escherichia coli.* More preferably, *Escherichia coli* BL21 (DE3).

When used as a biocatalyst for the production of EGT, the oxidative sulfurizing enzyme of the present invention may be in the form of enzyme or a form of host cells. The forms of the enzyme include free enzyme, immobilized enzyme, purified enzyme, crude enzyme, fermentation broth, carrier-immobilized enzyme, and the like; the forms of the host cell include living cell and dead cell.

General Method

Materials and Method

The separation and purification of the oxidative sulfide enzyme of the present invention, including immobilized enzyme preparation techniques, are also well known to those skilled in the art.

In the present invention, the whole gene synthesis in the present invention was done by a company named Genewiz, Inc. in Suzhou, China; the expression vector was prepared by subcloning of Zhejiang Huarui Biotechnology Co., Ltd. Primer synthesis and sequencing were performed by Genewiz, Inc. Molecular biology experiments include plasmid construction, restriction enzyme digestion, ligation, competent cell preparation, transformation, medium preparation, etc., mainly refer to "Molecular Cloning: A Laboratory Manual" (Third Edition), J. F. Sambrook, D. W. Russell edited, translated by Huang Peitang et al., Science Press, Beijing, 2002). Specific experimental conditions can be determined by simple tests if necessary. PCR amplification experiments were performed according to the reaction conditions or kit instructions provided by the plasmid or DNA template supplier. It can be adjusted by simple experiment if necessary.

Culture Medium and Buffer:

LB medium: 10 g/L tryptone, 10 g/L sodium chloride, 5.0 g/L yeast extract (solid medium added 20 g/L agar powder), pH 7.2, autoclaved at 121° C. for 20 min.

The fermentation medium (TB medium): 24 g/L yeast extract, 12 g/L tryptone, 16.43 g/L $K_2HPO_4 \cdot 3 H_2O$, 2.31 g/L $KH_2PO_4$, 5 g/L glycerol, pH 7.0-7.5, autoclaved at 121° C. for 20 min.

In the following examples, when an antibiotic-containing medium was used, the final concentration of the antibiotic was 50 μg/ml kanamycin. The corresponding antibiotic was added according to the characteristics of the transformed plasmid.

20×electrotransfer stock solution: 80 g/L glycine, 2% Tween 80.

HPLC Detection of EGT:

Detection conditions: Agilent high performance liquid chromatography 1260 infinity II, Elite ODS-BP column, column temperature 40° C., mobile phase: A, ammonium dihydrogen phosphate (configuration method, take 1.1503 g of ammonium dihydrogen phosphate+400 mL of purified water, adjust the pH with ammonia to 5.0, and add 100 mL of purified water); B:acetonitrile. A:B=99:1, the flow rate is 1 mg/min, the injection volume is 10 μL, and the detection wavelength is 258 nm.

EanB Reaction Assay System:

50 mM phosphate buffer, pH 8.0, 50 mM sodium thiosulfate, 200 mM sodium chloride, 1 mM TMH, 50 μM EanB protein (about 10 mg/ml after purification), 16 hours, 25° C.

Definition of enzyme activity: The enzyme amount required to catalyze the production of 1 micromolar (μmol) of EGT per minute at pH 8.0 and 25° C. is defined as one unit (U).

Example 1. Construction of Oxidative Sulfide Enzyme Expression Strain

SEQ ID NO: 2 was obtained by the whole gene synthesis, the restriction enzyme sites NdeI and BamHI were designed at two ends respectively. The sequence was then cloned into the corresponding sites on the pSH plasmid to obtain the recombinant plasmid pSH-EanB, which was then transformed into *E. coli* expressing strain BL21 (DE3) by electroporation. The cells were cultured overnight at 37° C. on the LB plate coating with 50 μg/ml kanamycin.

Single colonies were selected from the plate and seeded into LB medium with 50 μg/ml kanamycin, after cultured overnight, the cells were collected by centrifugation. The plasmid was extracted and the gene was sequenced correctly, the recombinant strain BL21(DE3)/pSH-EanB expressing wild-type EanB was obtained. The amino acid sequence was determined as SEQ ID NO: 1.

Single colonies were selected from the above plate and inoculated into 5 mL LB medium with 50 μg/ml kanamycin at 37° C. Then, 1% v/v of culture medium was inoculated into 1000 mL flask containing 100 mL fermentation medium, after culturing for 4-6 hours, the $OD_{600}$ reached 1.2-1.5, the recombination strain was induced by final concentration 0.2 mM of IPTG, and was incubated at 25° C. for 10-16 hours. The cells were obtained by centrifugation and frozen at −80° C. for 24 hours backup.

Example 2. Construction of eryK Random Mutation Library by Error-Prone PCR

A random mutation library was constructed by error-prone PCR using SEQ ID NO: 2 as template.

```
Forward primer (EanB-Nde-F):

5'-CATATGCAGAACAAAAACTTTCG-3',

Reverse primer (EanB-Bam-R):
5'-GGATCCTTATTTAGGCACGCCGGTTT-3'.
```

The 50 μL error-prone PCR reaction system includes: 50 ng plasmid template pSH-EanB, 30 pmoles of primer EanB-Nde-F and EanB-Bam-R, 1×Taq buffer, 0.2 mM dGTP, 0.2 mM dATP, 1 mM dCTP, 1 mM dTTP, 7 mM MgCl$_2$, (0 mM, 0.05 mM, 0.1 mM, 0.15 mM, 0.2 mM) MnCl$_2$, 2.5 unit of Taq polymerase (Fermentas). The PCR reaction condition was: 95° C. for 5 min; 94° C. for 30 sec, 55° C. for 30 sec, 72° C. for 2 min/kbp, 30 cycles; 72° C. for 10 min. The 1347 bp random mutant fragment was recovered by gel extraction as a large primer, and the MegaPrimer PCR was performed with KOD-plus DNA polymerase. The PCR condition was: 94° C. for 5 min; 98° C. for 10 sec, 60°. for 30 sec, 68° C. for 2 min/kbp, 25 cycles; 68° C. for 10 min. The plasmid template was digested with DpnI and electroporated into *E. coli* BL21 (DE3) to obtain more than 10$^4$ clones of a random mutation library.

Example 3. High Throughput Screening of EanB Mutant Library

The transformants in the EanB mutant library were selected and inoculated into 96-well deep-well culture plates containing 700 μL LB medium with 100 m/mL kanamycin. After incubation for 6 hours at 37° C., final concentration of 0.1 mM IPTG was added. And then the temperature was lowered to 25° C. for overnight incubation. After centrifugation at 5000 rpm for 10 min, the supernatant was discarded, and then frozen at −70° C. for 1 hours, and thawed at room temperature for 30 min. 200 μL of 0.1M potassium phosphate buffer (pH 7.4) was added to resuspend the cells for EanB enzyme activity assay.

80 μL cell suspension (i.e., the enzyme solution) in the above step was added to 80 μL substrate reaction solution (50 mM phosphate buffer, pH 8.0, 50 mM sodium thiosulfate, 200 mM sodium chloride, 1 mM TMH). After reacted at 37° C. for 2 hours, 40 μL termination solution (0.5 ml of a 1M NaOH solution) was added to terminate the reaction, and then centrifuged at 5000 rpm for 10 minutes. The supernatant was taken and detected by HPLC to calculate the EanB enzyme activity.

In the random mutation library, four mutant sites for enhancing the activity of EanB enzyme were got by screening about 1000 mutant clones, and the results are shown in Table 1.

For determination and screening of high activity EanB enzyme mutants, the enzyme activities of the respective EanB mutants were screened and determined repeatedly according to the methods described above.

TABLE 1

Comparison of enzyme activities of some EanB mutants

| Strain No. | Mutant site | Enzyme relative activity (%)* |
|---|---|---|
| EanB | — | 100 |
| EanB-19 | I75R | 320 |
| EanB-665 | K84L, E369P | 195 |
| EanB-888 | I75R, E369P | 480 |

*Enzyme relative activity: The ratio of the wild-type EanB enzyme activity is set to 100% as control.

The amino acid sequence of the EanB-888 mutant is SEQ ID NO: 3, the corresponding nucleic acid sequence is SEQ ID NO: 4. The amino acid sequence of the EanB-19 mutant is SEQ ID NO: 5, the corresponding nucleic acid sequence is SEQ ID NO: 6. The amino acid sequence of the EanB-665 mutant is SEQ ID NO: 7, the corresponding nucleic acid sequence is SEQ ID NO: 8.

The enzyme activity of the mutant strain numbered EanB-888 (I75R, E369P) shows the highest enzyme specific activity, which is 4.8-fold higher than that of wild-type enzyme EanB.

Thus, the EanB-888 mutant may be suitable for mass production of EGT.

Example 4. Construction of High Enzyme Activity Genetic Engineering Microbial Cell The SEQ ID NO: 4 of the EanB-888 mutant was cloned into the pSH plasmid according to the method of Example 1 to obtain a recombinant plasmid pSH-EanB-888, which was then transformed into *E. coli* BL21 (DE3) by electroporation. The cells were cultured overnight on the LB plate coated with kanamycin at 37° C. 10 single colonies were selected and inoculated into tubes containing LB medium, after cultured overnight, the cells were collected by centrifugation. The plasmid was extracted, and the gene was sequenced correctly, and then the recombinant strain was obtained.

It will be understood by those skilled in the art that the EanB-888 mutant encoding gene including SEQ ID NO: 4 can also be expressed in *Bacillus subtilis, Pichia pastoris, Saccharomyces cerevisiae*, and the expression host is not limited to *E. coli*.

Example 5. Fermentation of EanB Wild-Type and EanB-888 Mutant Strain

Single colonies were selected from the plates of wild type strain and mutant strain, and then inoculated into 5 mL of LB medium at 37° C. Then, 1% v/v of medium was inoculated into 1000 mL flask containing 100 mL of TB medium. After culturing for 4-6 hours, the OD$_{600}$ reached 1.2-1.5, the cells were induced by adding final concentration of 0.2 mM IPTG, and were incubated at 25° C. for 10-16 hours. The cells were obtained by centrifugation and frozen at −80° C. for 24 hours backup.

Example 6 the EanB-888 Mutant Catalyzes the Formation of EGT by TMH

The reaction system was 200 mL, the substrate TMH concentration was 10 g/L, and the amounts of added enzyme were 2000, 4000, 6000, 8000, 10000 U/g substrate, respectively. The reaction conditions were at 37° C., 200 rpm, pH 8.0, reacting for 24 hours. The EGT production amount was measured, and the substrate conversion rate was calculated. The results are shown in Table 2.

TABLE 2

Preparation of EGT by TMH catalyzed by adding different amounts of mutant enzyme EanB-888.

| TMH (g/L) | Enzyme amount (U/g substrate) | Conversion rate (%) |
|---|---|---|
| 10 | 2000 | 5.3 |
|  | 4000 | 8.5 |
|  | 6000 | 16.4 |
|  | 8000 | 33 |
|  | 10000 | 34 |

From the table, it can be seen that the conversion rate already gets to 34% with the mutant enzyme amount of 10000 U/g substrate in 24 hours.

According to the table, it can easily get the conclusion that, the mutant EanB-888 make it possible for mass production of EGT.

The above examples demonstrate the process of producing EGT by the mutant enzyme EanB of the present invention, and the relevant process conditions can be further optimized. It should be understood by those skilled in the art that various changes and modifications may be made by those skilled in the art without violating the idea of the present invention.

The invention claimed is:

1. An EanB enzyme mutant comprising mutation of one or more changes at position 75, 84 or 369 in amino acid sequence of SEQ ID No 1, wherein the mutation is one or two of following changes: (1) I of position 75 is mutated to R; (2) E of position 369 is mutated to P.

2. The EanB enzyme mutant according to claim 1, wherein the mutant comprises an amino acid sequence of SEQ ID NO: 3, SEQ ID NO: 5, or SEQ ID NO: 7.

3. The EanB enzyme mutant according to claim 2, wherein the EanB enzyme mutant is encoded by a polynucleotide, wherein the polynucleotide comprises a nucleic acid sequence of SEQ ID NO: 4, SEQ ID NO: 6, or SEQ ID NO: 8.

4. The EanB enzyme mutant according to claim 3, wherein the polynucleotide is located on an expression vector.

5. The EanB enzyme mutant according to claim 4, wherein the expression vector is pSH plasmid.

6. The EanB enzyme mutant according to claim 3, wherein the polynucleotide is included in a host cell.

7. The EanB enzyme mutant according to claim 6, wherein the host cell is *Escherichia coli*.

8. An EanB enzyme mutant comprising mutation of one or more changes at position 75, 84 or 369 in amino acid sequence of SEQ ID No 1, and further comprising an amino acid sequence of SEQ ID NO: 3, SEQ ID NO: 5, or SEQ ID NO: 7.

9. The EanB enzyme mutant according to claim 8, wherein the EanB enzyme mutant is encoded by a polynucleotide, wherein the polynucleotide comprises a nucleic acid sequence of SEQ ID NO: 4, SEQ ID NO: 6, or SEQ ID NO: 8.

10. The EanB enzyme mutant according to claim 9, wherein the polynucleotide is located on an expression vector.

11. The EanB enzyme mutant according to claim 10, wherein the expression vector is pSH plasmid.

12. The EanB enzyme mutant according to claim 9, wherein the polynucleotide is included in a host cell.

13. The EanB enzyme mutant according to claim 12, wherein the host cell is *Escherichia coli*.

* * * * *